(12) United States Patent
Völker et al.

(10) Patent No.: US 11,654,396 B2
(45) Date of Patent: May 23, 2023

(54) REVERSE OSMOSIS SYSTEM AND METHOD OF OBTAINING ULTRAPURE WATER

(71) Applicant: FIDICA GmbH & Co. KG, Sailauf (DE)

(72) Inventors: Manfred Völker, Blankenbach (DE); Thomas Reinhart, Niedernberg (DE)

(73) Assignee: FIDICA GMBH & CO. KG, Sailauf (DE)

( * ) Notice: Subject to any disclaimer, the term of this patent is extended or adjusted under 35 U.S.C. 154(b) by 108 days.

(21) Appl. No.: 16/942,361

(22) Filed: Jul. 29, 2020

(65) Prior Publication Data

US 2021/0362093 A1 Nov. 25, 2021

(30) Foreign Application Priority Data

May 22, 2020 (DE) .......................... 202020102937.1

(51) Int. Cl.
*B01D 61/02* (2006.01)
*B01D 61/08* (2006.01)
(Continued)

(52) U.S. Cl.
CPC ......... *B01D 61/025* (2013.01); *A61M 1/1672* (2014.02); *B01D 61/026* (2022.08);
(Continued)

(58) Field of Classification Search
CPC ............ B01D 61/025; B01D 2311/103; B01D 2313/083
See application file for complete search history.

(56) References Cited

U.S. PATENT DOCUMENTS

| 8,790,513 B1 * | 7/2014 | Boulter ..................... C02F 9/00 |
| | | 210/104 |
| 10,099,179 B2 | 10/2018 | Volker | |
| 2007/0295673 A1 * | 12/2007 | Enis ......................... C02F 1/22 |
| | | 210/170.11 |

(Continued)

FOREIGN PATENT DOCUMENTS

CN  202808519 U  *  3/2013
DE  10013964 A1  *  9/2001  .......... A61M 1/1656
(Continued)

OTHER PUBLICATIONS

Chen B—CN-202808519-U machine translation—2013 (Year: 2013).*
(Continued)

*Primary Examiner* — Bradley R Spies
(74) *Attorney, Agent, or Firm* — Greer, Burns & Crain, Ltd.

(57) ABSTRACT

The reverse osmosis system with at least one high pressure pump, which supplies untreated water to at least one module pipe, in which a membrane with a permeate collecting pipe is arranged, includes a permeate outlet of the at least one module pipe that is connected by means of a first conduit to a permeate tank, which is in communication by means of a further conduit, connected into which there is a permeate supply pump, with a loop feed line, to which a plurality of dialysis devices are connected and that branching off from the first conduit there is a bypass conduit, which discharges into the further conduit downstream of the permeate tank and the permeate supply pump.

11 Claims, 5 Drawing Sheets

(51) Int. Cl.
  *B01D 61/10* (2006.01)
  *C02F 1/44* (2023.01)
  *A61M 1/16* (2006.01)

(52) U.S. Cl.
  CPC ............ *B01D 61/08* (2013.01); *B01D 61/10* (2013.01); *C02F 1/441* (2013.01); *B01D 2311/06* (2013.01); *B01D 2311/20* (2013.01); *B01D 2313/083* (2013.01); *B01D 2313/12* (2013.01); *B01D 2313/18* (2013.01); *B01D 2313/19* (2013.01); *B01D 2313/243* (2013.01); *C02F 2201/007* (2013.01)

(56) References Cited

U.S. PATENT DOCUMENTS

| | | | | |
|---|---|---|---|---|
| 2009/0134080 | A1* | 5/2009 | Fabig | C02F 1/441 210/181 |
| 2013/0075310 | A1* | 3/2013 | Volker | B01D 61/08 210/85 |
| 2014/0151309 | A1* | 6/2014 | Schreiner | B64D 11/00 137/565.17 |
| 2019/0010681 | A1* | 1/2019 | Shi | E03B 11/08 |
| 2019/0071327 | A1* | 3/2019 | Feilner | B01D 61/08 |

FOREIGN PATENT DOCUMENTS

| | | |
|---|---|---|
| DE | 10013964 A1 | 9/2001 |
| DE | 10111104 A1 | 10/2002 |
| DE | 102009057562 A1 | 6/2011 |
| EP | 2181965 A1 | 5/2010 |
| EP | 2865651 A1 | 4/2015 |
| WO | WO0189996 A2 | 11/2011 |

OTHER PUBLICATIONS

Walther P—DE-10013964-A1 machine translation—2001 (Year: 2001).*
European Search Report dated Nov. 23, 2020 for European Application No. EP 20 18 1069.

* cited by examiner

REVERSE OSMOSIS SYSTEM AND METHOD OF OBTAINING ULTRAPURE WATER

FIELD OF THE INVENTION

The invention relates to an apparatus for the treatment of water on the reverse osmosis principle. Apparatus of this type, reverse osmosis or RO systems, are used in particular in connection with haemodialysis devices in order to obtain sufficiently pure, sterile water from tap water for the preparation of dialysis liquid.

SUMMARY OF THE INVENTION

The invention aims in particular at savings in resources in the form of electrical energy and untreated water in operation of the reverse osmosis and also the dialysis machines. Further objectives are expected, however, also to reside in minimal space requirements and also in reliability of the ultrapure water supply.

This object is solved by the features of the main claim. Further features and embodiments will be apparent from the dependent claims and the following description of exemplary embodiments in conjunction with the drawings, in which:

DETAILED DESCRIPTION OF PREFERRED EMBODIMENTS

Figure 1:
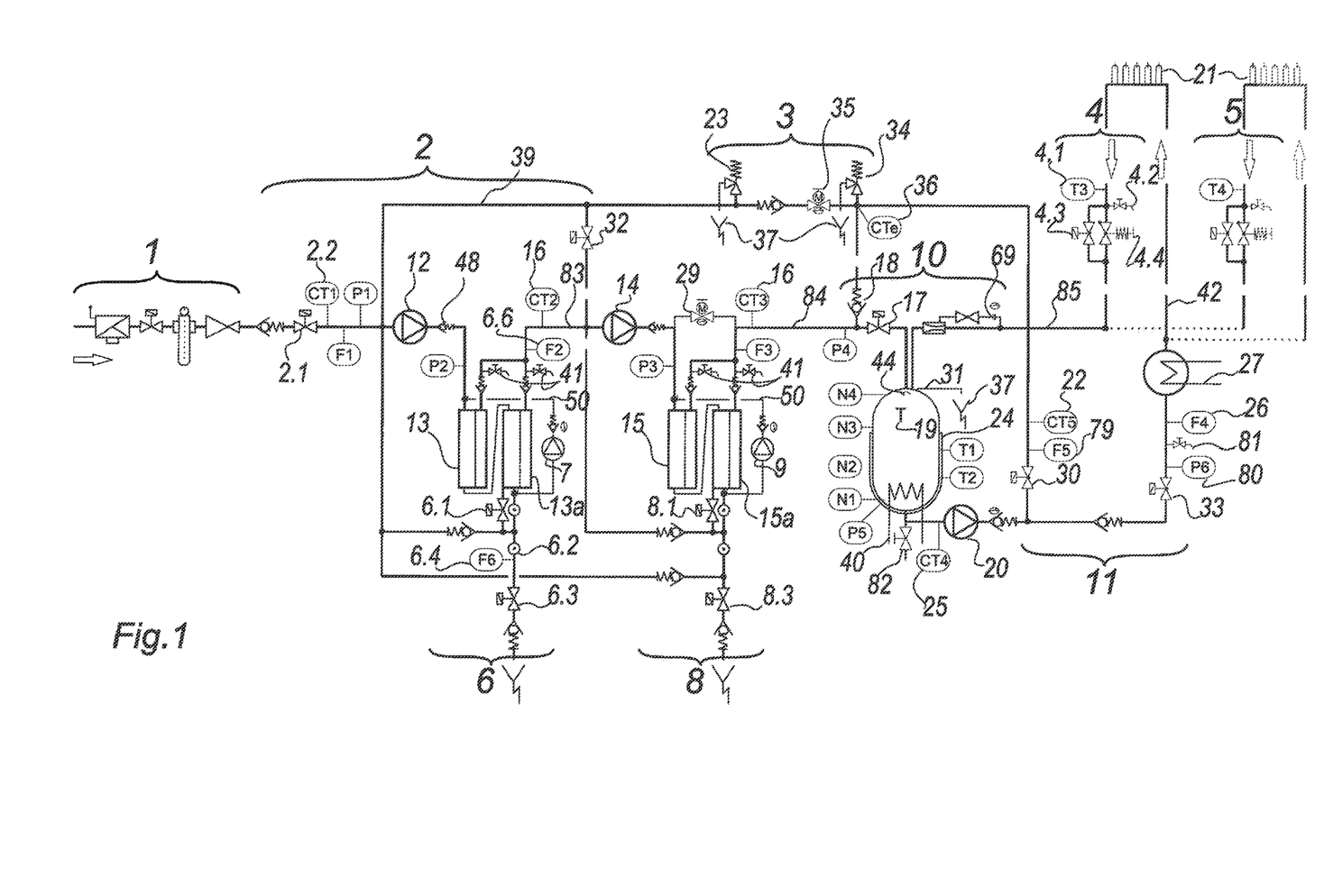
FIG. 1 is a schematic diagram of a reverse osmosis system with the equipment features in accordance with the invention.

In the schematic diagram of the reverse osmosis system in accordance with the invention, it is in particular the arrangement of the main subassemblies which are used, their structural arrangement and the cooperation with actuators and sensors which achieve a considerable resource saving in all program steps—supplying the dialysis device with ultrapure water, cleaning the loop line, cleaning the reverse osmosis system.

The diagrammatic drawing shown in FIG. 1 illustrates the interaction of the important main subassemblies. It will be shown with reference to the diagrammatic drawing how the saving in resources is achieved in the program steps.

A reverse osmosis system in accordance with the prior art operates when supplying the dialysis devices with ultrapure water, either in tank operation, i.e. an ultrapure water tank is filled in start-stop operation, and a permeate distribution pump supplies the dialysis devices from the tank or the reverse osmosis system conveys the ultrapure water directly to the dialysis devices.

Both variants of the method are not optimal as regards the actual dialysis operation, in which the number of the connected treatment units can vary considerably depending on the day of the week and the time of the day.

On the one hand, the tank volume and the storage capacity of the reverse osmosis system should be matched to an optimal working point, which, when utilisation fluctuates, results either in a frequent Start/Stop operation or in long production downtimes of the reverse osmosis system with the risk of microbial contamination. Reverse osmosis systems for direct supply can compensate for low utilisation only unsatisfactorily despite control of the efficiency because e.g. the pumps are to be designed for the maximum output.

The tank is therefore advantageously limited in its volume to a maximum of 200 l. Thus e.g. the reverse osmosis system can convey ultrapure water to the dialysis devices with an additional permeate distribution pump with a possible supply of 50 treatment units and a reverse osmosis capacity of ca. 2500 l/h without a Start/Stop operation via the tank. Slightly varying amounts being removed are to be compensated for by the tank supply being closed when an upper tank filling level is reached and excess permeate is conveyed back to the inlet of the reverse osmosis system. With minimal amounts being removed, e.g. when supplying only a few treatment units with ultrapure water—basically however, at ca. 30% of the rated output the reverse osmosis system is switched into tank operation, i.e. Start/Stop operation. The aforementioned output in the amount of 30% of the rated output is a value derived from real dialysis operation. With ca. 5000 annual operating hours of a reverse osmosis system with ca. 2500 l/h in dialysis operation ca. 22000 treatments are possible. Experience shows that ca. 50% is produced at rated output and ca. 50% at merely 30% of the rated output.

Whilst the pumps of a standard reverse osmosis system produce their full output for the duration of a dialysis treatment even in partial load operation and have a concentrate flow despite control of efficiency even with low amounts being removed, the pumps and the concentrate flow are stopped in accordance with the invention when the tank is full and the dialysis devices are supplied by means of a permeate distribution pump, which requires a lower power.

With an assumed reverse osmosis capacity of ca. 2500 l/h and water prices of ca. 5 €/m$^3$, an electricity price of 0.30 €/kWh and ca. 2500 operating hours p.a. with treatment units reduced to ca. 30%, this results in annual savings of ca. 5 K€ in electricity (2 pumps at 4.2 kW/h×2000 h×0.3 €/kWh) and 5 K€ in water (0.5 m$^3$×2000 h×5€/m$^3$), that is to say altogether ca. 10K€ p.a.

The electrical heating power of a dialysis machine for the preparation of the dialysis liquid/dialysis treatment is 5.12 kWh at a temperature increase of ca. 15° C. to 37° C. With the aforementioned operational data and a typical water consumption of ca. 200 l per dialysis treatment and ca. 22000 treatments p.a., this adds up to ca. 100,000 kWh p.a. The object of the invention is to replace the electrical energy which is required for the preparation of the dialysis liquid at least partially by primary energy (oil, gas, sun, wind).

In a price comparison with the use of electrical energy, a saving effect is produced with respect to the electrical costs of up to 32K€ p.a. by means of heat transfer by primary energy into the tank and/or by additional heat exchangers in the loop line for the permeate, depending on the nature of the primary energy (oil, gas; sun). (5.12 kWh per treatment:4 hours/treatment=1.28 kW×48 treatment units=61.44 kW required primary energy). This heat input can be realised in practice, by primary energy, depending on the size of the tank wholly or partially into the tank (double walled and/or heat exchangers) or additional further annular heat exchangers. As a further possibility, the supply of the electrical tank heaters, which will be described below, with primary energy can be considered.

The illustrated reverse osmosis system is of two stage type. On the one hand to achieve as high as possible a quality of the ultrapure water and on the other hand to maintain the security of supply to the treatment units in the event of failure of one stage. Furthermore, in the event of a defect occurring to electrical, hydraulic or mechanical components, the first or the second stage can be operated individually without the electronic main controller. The start of the emergency operation is effected by a key switch, which activates a relay switch independent of the main controller, connected to which is an independent conductivity and temperature monitoring device and valve circuit also independent of the main controller.

The overflow on the primary side is of considerable significance for the function of the RO membranes. The operational conditions of the membranes are to be so set, having regard to the quality of the untreated water, that the concentrate flow over the primary side is a multiple of the permeate flow conveyed to the dialysis devices. The pressure necessary for the membrane filtration and the conveying of the permeate is produced by the reverse osmosis pumps. Circulation pumps can advantageously be provided between the primary inlet and primary outlet (concentrate outlet) of the membranes in order to achieve an optimal overflow and thus a long service life of the membranes. The even more important advantage resides in the power consumption, which is reduced by ca. 70% by comparison with a reverse osmosis system without circulation pumps. With the aforementioned rated output, 2 pumps of 4.2 kW/h are typically used. With 5000 operational hours and 0.3 €/kWh approximately ca. 8K€ p.a. are saved.

FIG. 1 shows a two-stage RO, which is equipped both in the first and also the second stage with two respective membranes (13/15) to double the output. The supplied untreated water is conducted via an inlet valve (2.1) and the conductivity meter (2.2) to the pump (12) and, in the form of highly pure permeate from the first stage (83), reaches the pump (14), which conducts highly pure permeate via membrane (15) into the permeate tank (19) via a conduit (84), the tank release valve (17) and the tank inlet (44).

The highly pure permeate is conducted from there to the dialysis devices (21) via pump (20), pressure monitor (80), sample removal (81), flow meter (26) and conduit (42). Excess permeate can be conducted back into the tank (19) via the return flow units (4/5), a pressure-retaining valve (4.4), further sample removal valve (4.2) and temperature sensor (4.1). Valve (4.3) opens when required in order to relieve the pressure retention of the loop, e.g. in cleaning programs. Return flow unit (5) is of identical construction if a second permeate supply conduit is installed.

In the event of appropriately large permeate removal volumes by the dialysis devices (21), tank (19) is used merely as a flow through unit. In the event of smaller removals, switching off of the valve (17) is possible in dependence on the four level switches on the tank, whereby the permeate can flow back via conduit (39) to the pump (12). The pumps (12/14) are, however, advantageously switched off—in order to save energy/water—until the level switch of the tank (19) registers a renewed requirement.

The permeate produced, which is used via conduit (42) for the preparation of the dialysis liquid for dialysis devices (21), can be pre-heated nearly to the necessary temperature for the preparation of the dialysis liquid by means of primary energy by way of heat exchangers (24/27) and/or electrical heaters (40)—also by means of primary energy—in order to save electrical heating energy of the dialysis devices. For this purpose, the said actuators and sensors in the functional unit (11) and also recirculation via conduit (42) and tank (19) by means of pump (20) and the monitor (25) are necessary.

In order that the pumps (12/14) need apply a minimum of electrical power, their capacity is so designed that efficient operation with low discharge via valves (6.3 and 8.3) and the maximum necessary permeate volume is possible. The constant overflow on the primary side, which is necessary for the membranes (13/15), is ensured exclusively by means of circulation pumps (7.9).

In the event of failure of the reverse osmosis system, for instance of the first stage (12/13), the untreated water is conducted via valve (32) to pump (14) and from there it can flow in loop conduit (42) with a pump (20) functioning. In the event of failure of pump (20) there is alternatively the possibility of closing valve (17) to conduct the permeate in loop line (42) via overflow valve (18) and conductivity and temperature meter (36) and bidirectional valve (30), through which flow is in the opposite direction for the purpose of cleaning the membrane. Excess permeate flows back into tank (19) and goes via overflow (31) to discharge (37). In this event, the motor-driven valve (35) is closed and in the event of failure of stage 2 (14/15) the permeate is conducted via the opened, motor-driven valve (29) and the previously described method to the dialysis devices. Valves (29/35) should also be actuated manually.

The conductivity and temperature meter (36) and valves (30/33) can be operated independently of the main controller in order to ensure reliable emergency operation. Valve (30) is to be safely operated bidirectionally in order to perform, on the one hand, the emergency operation, and, on the other hand, the cleaning of the membranes with hot water.

In order to clean the permeate supply conduit (42/85), the tank volume is heated up electrically by means of heater (40) or by means of primary energy. There is also alternatively the possibility of warming by means of heat exchangers (24/27). Pump (20) circulates the warmed permeate to the necessary temperature, which is registered by means of temperature sensors (25/4.1). Flow meter (26) serves as a monitor, for instance for leakage protection or removals by the dialysis devices (21).

In order to clean the membranes, the permeate located in the tank (19) is, as described above, heated. Valve (33) closed; the bidirectional valve (30) opened, pump (20) conveys the permeate selectively via valve (32) to the $2^{nd}$ stage or to the pump (12) of the $1^{st}$ stage and via this to the $2^{nd}$ stage. The stages can thus selectively be hot cleaned independently or together. For this purpose, the high pressure bypass valves (6.1/8.1) are opened, the pumps (12/14) operated at low pressure in a manner which preserves the membranes, either in a speed controlled manner or, with great advantage, switched over to rotate in the opposite direction in order to achieve a low concentrate pressure. After a short flushing process of the membrane primary sides (13/15), the discharge valves (6.3 and 8.3) are closed. Pumps (7 and 9) circulate.

In order to perform a chemical or chemo-thermal disinfection of the RO system, disinfectant can be metered via suction plugs (69) and introduced into tank (19) by means of Venturi or other metering pumps. It is moved from there via loop line (42) or alternatively, when loop line (42) is blocked, via the bidirectional valve (30) to the RO in order to be distributed there.

The remaining volume in the tank (19) is diluted by the supply of fresh permeate and conveyed via valve (34) to the discharge. In addition to electrical actuation, valve (34) also has a mechanical overflow in order to protect the line (42) from an overpressure, for instance when providing an emergency supply.

Figure 2:
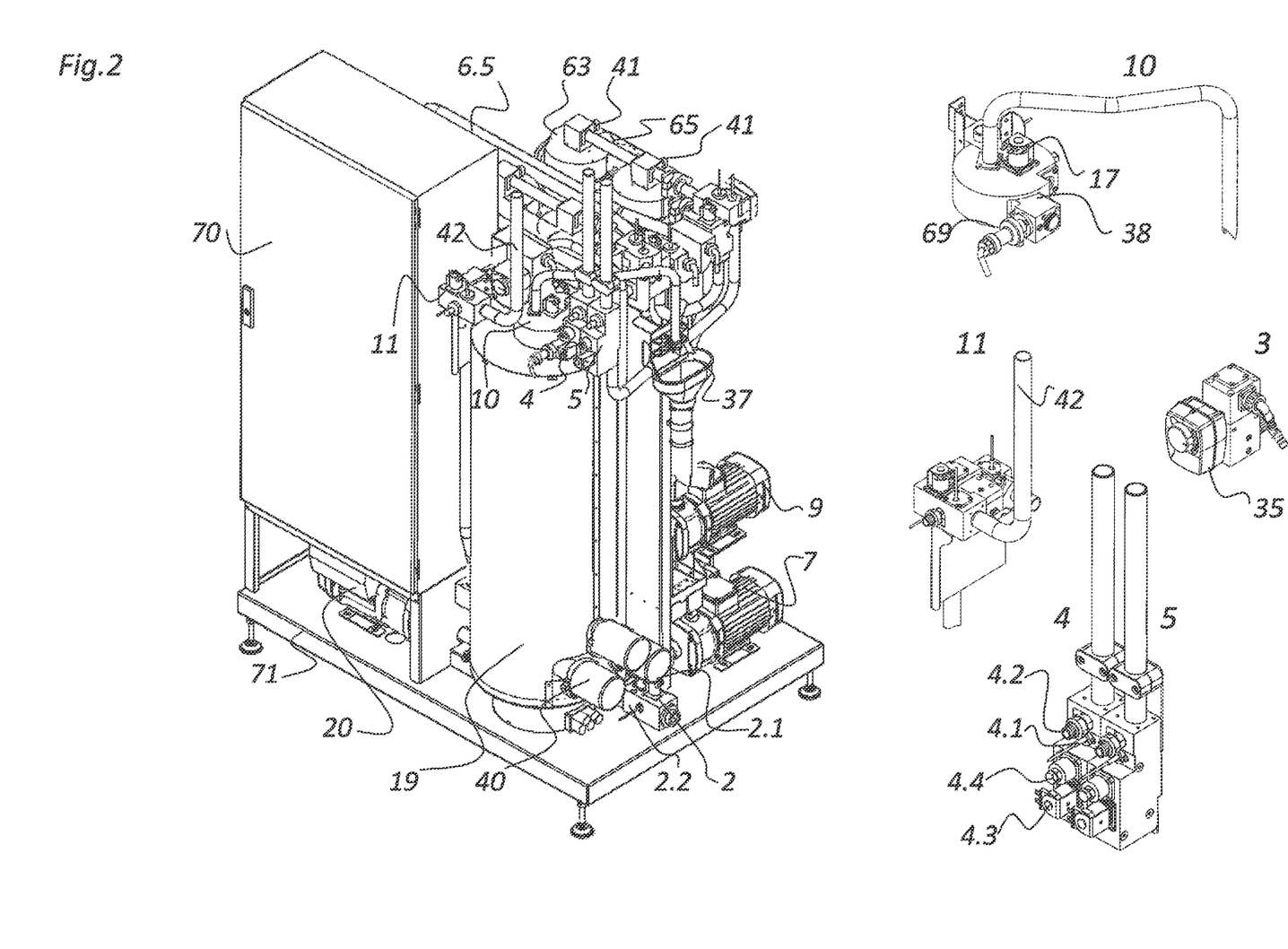
FIGS. 2-2.6 show embodiments of important subassemblies in accordance with the invention.
Figure 21:
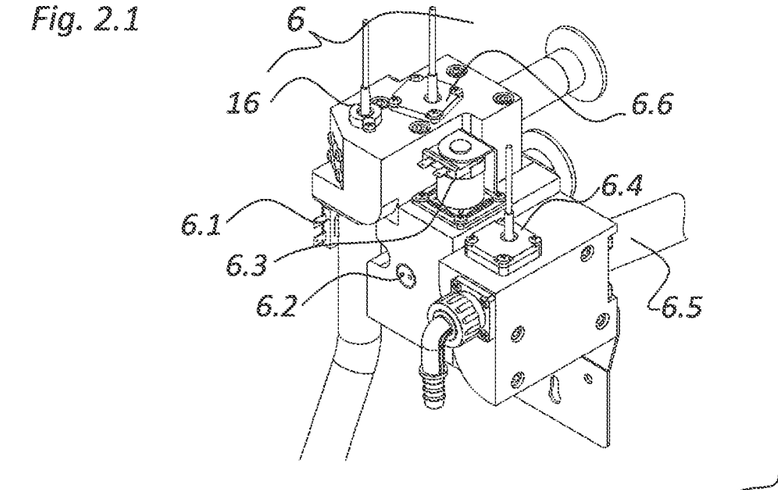

Valve (23) also protects the system from excessive inlet pressure of the untreated water. FIG. 2 is a perspective view of the RO system in order to illustrate the spatial construction and the compactness. With a length of ca. 1200 mm, a breadth of ca. 900 mm and a height of ca. 1700 mm, palette dimensions are nearly achieved and the system is thus able to pass through doors, has low installation dimensions and low freight costs. The illustrated two-stage system produces ca. 2300-2500 litres ultrapure water per hour. By way of example, a few of the at most 15 subassemblies are also shown in FIG. 2.1 in order to illustrate the compactness.

Figure 22:
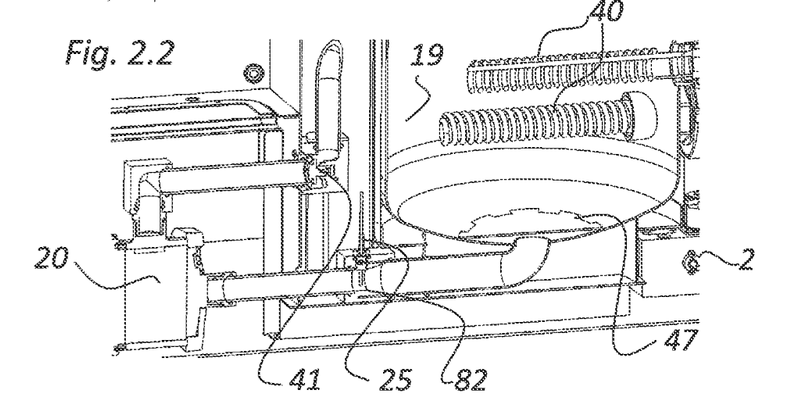

FIG. 2.2 shows a few details of the tank (19) with the laterally attached heaters (40) and the cyclone preventer (47), installed above the base drain, which is necessary with a pump (20) with strong suction, low filling levels in the tank (19) and high temperatures of the liquid. The cyclone preventer avoids the introduction of air into the pump (20) and into the system.

Figure 23:
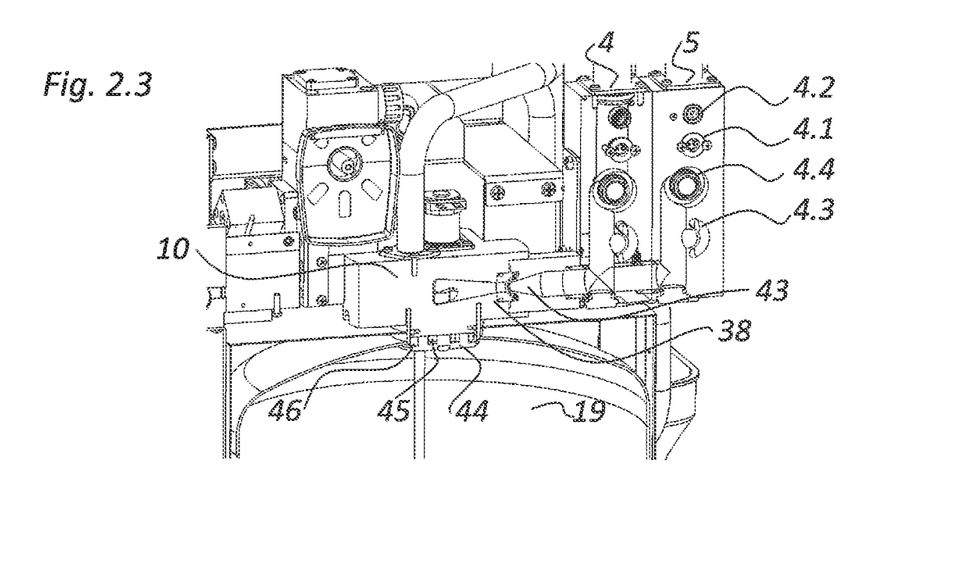

FIG. 2.3 is a sectional view of the tank inlet block (10). Not illustrated is the venting bore, which is located in the middle of the tank inlet block (10) and which conducts air or overflowing liquid via conduit (31) to the discharge (37). Both the permeate flowing in and also the permeate flowing back is advantageously conducted in the tank inlet (44) by way of radially arranged outlet passages (45) into an annular outlet groove (46) so that the inner wall of the tank is wetted over its entire area and can be flushed without any dead space. Also not illustrated is an additional access mounted in the tank cover for a float switch with at least 4 contact signals.

Figure 24:
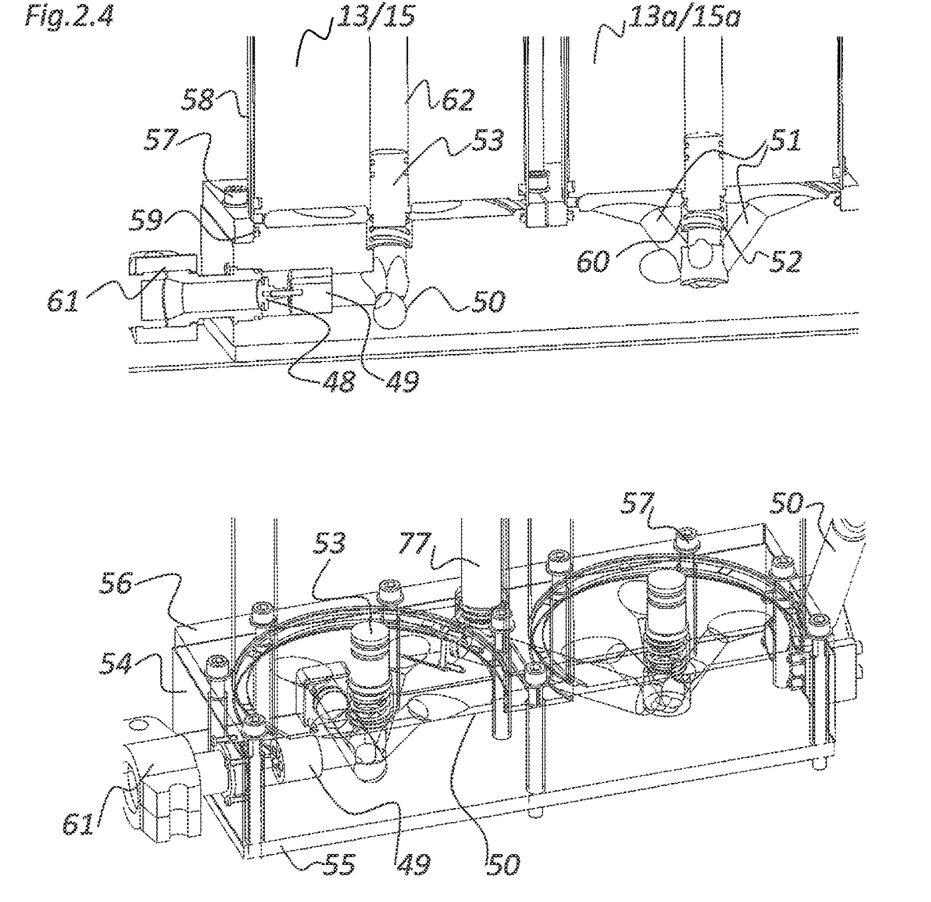

FIG. 2.4 shows the module block (54) with the module pipes (58) fastened thereon and the membranes (13/15) situated therein. The thin-walled module pipe (58) is welded to a prismatic flange plate (56) and is screw-connected to the module base plate (55) with screws (57). For the purpose of sealing, a sealing ring (89) is situated in a peripheral groove in the module block (54) and seals against the sealing surface, which is cut out and machined internally in a circular shape, of the flange plate (56). For this purpose, the thickness of the material of the flange plate must be greater than at least 10 mm.

The permeate collecting pipe (62) is closed at the bottom by means of plug (53) and is mounted floatingly with supporting springs (52) in order to compensate for hydraulic shocks and to absorb expansion of the material of the membranes (13/15). The untreated water supply by means of pump (12) can be effected via non-return valve (48) and inlet flow distributor (49) and is conducted via at least 4 circularly arranged oblique bores (51) onto the lower end surface of the membrane.

The conduit (50) of the circulation pumps (7/9) is also routed in the module block (54).

Figure 25:
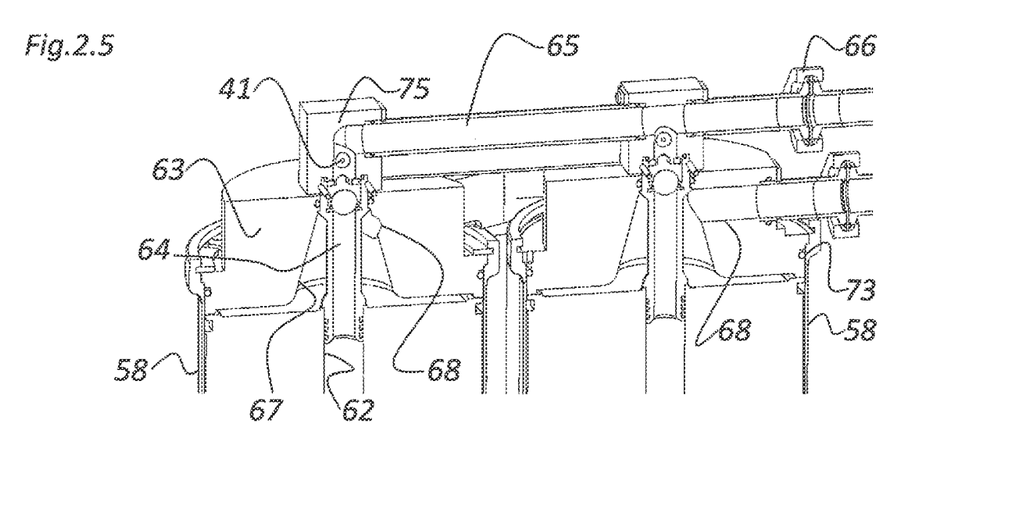
Figure 26:
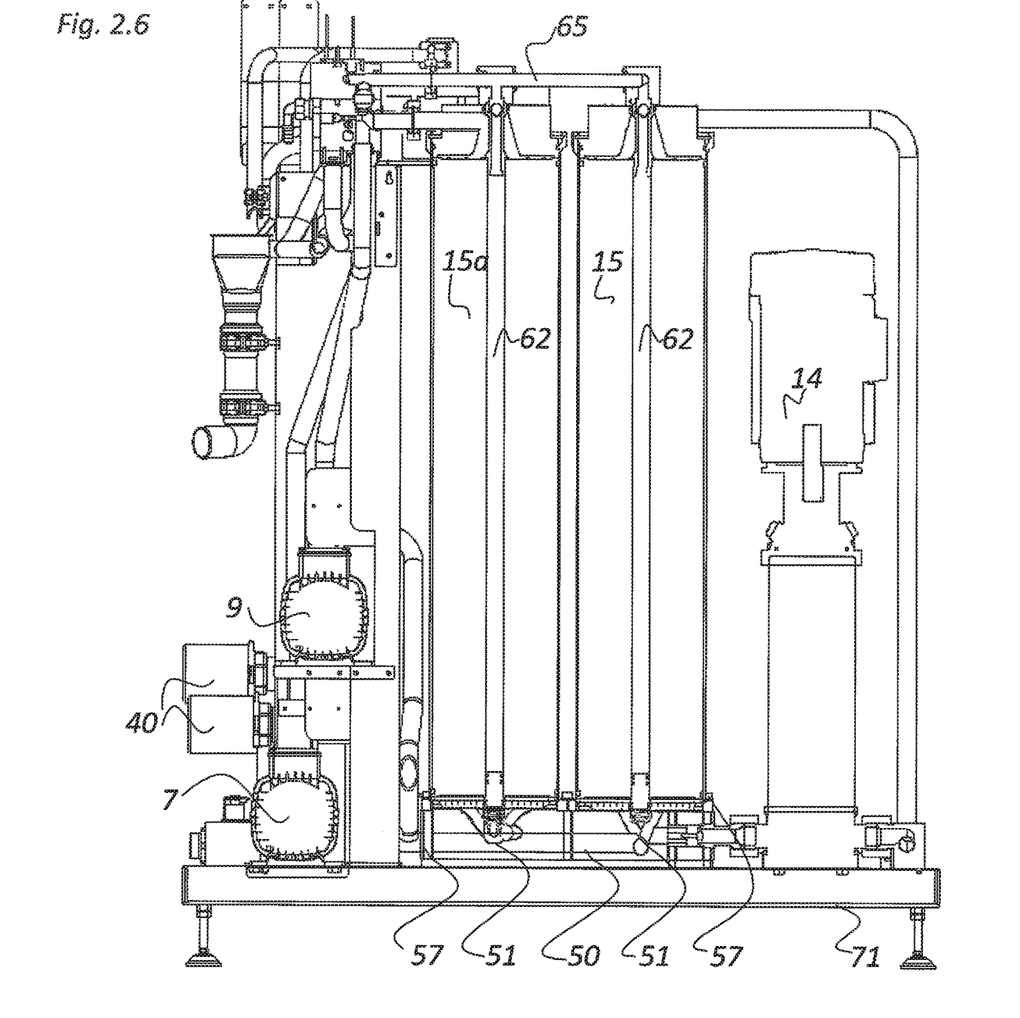

FIGS. 2.5 and 2.6 show the following:

The untreated water which is supplied is mixed with the liquid from the circulation pumps (7/9) and conducted through the spirally wound membranes and also by way of a bypass current in the annular gap (87), the pressure pipe inner surfaces and membrane outer surfaces.

FIG. 2.5 shows that the permeate produced by the membrane is conducted via permeate collector (62) to membrane non-return valve (64) in the module head (63). Membrane non-return valve (64) produces a sealing connection. Non-return valve (64) includes a ball (66) and seal (72) in order to protect the membrane from backflow.

FIG. 2.6 shows that the permeate collector and sample removal block (75) is plugged onto membrane non-return valve (64) and is secured thereto by means of cylinder pegs (89). A selective test for every membrane is possible by the sample removal (41) situated in the permeate collector and sample removal block (75). The permeate is conducted on from the permeate collector and sample removal block (75) via permeate connector (65).

Both the module block (54) and the module head (63) have milled areas (74) so that when the end surface of the membrane is in engagement the liquid can flow out of annular gap (47). The discharging concentrate is conducted away at the module head (63) via an inner cone (67) and outlet bore (68). Module head (63) has a peripheral groove (73) in which a sealing ring forms a seal against a machined surface on the flange (78). The fastening of the module head (63) can be effected by means of screw connections (not shown) or clamping to flange (78) and for this purpose a flange ring is layed over ledge (88) and screw-connected to the flange welded to the module pipe or a groove in the flange (78) accommodates locking washers on which the module head is positioned.

| | |
|---|---|
| 1 | Prefiltration unit |
| 2 | Water inlet group |
| 2.1 | Water inlet valve |
| 2.2 | Temperature and conductivity meter |
| 3 | Safety group |
| 4 | Return loop 1 |
| 4.1 | Temperature sensor return loop |
| 4.2 | Sample removal valve |
| 4.3 | Bypass valve |
| 4.4 | Pressure retaining valve |
| 5 | Return loop 2 |
| 6 | Functional unit $1^{st}$ stage |
| 6.1 | High pressure throttle with bypass valve |
| 6.2 | Discharge throttle |
| 6.3 | Discharge valve |
| 6.4 | Discharge flow meter |
| 6.5 | Concentrate circulation |
| 7 | Circulation pump $1^{st}$ stage |
| 8 | Functional unit $2^{nd}$ stage |
| 8.1 | High pressure throttle with bypass valve |
| 8.2 | Permeate circulation |
| 9 | Circulation pump $2^{nd}$ stage |
| 10 | Tank inlet group |
| 11 | Tank outlet group |
| 12 | High pressure pump 1 |
| 13 | Membrane $1^{st}$ stage |
| 14 | High pressure pump 2 |
| 15 | Membranes $2^{nd}$ stage |
| 16 | Temperature and conductivity sensors |
| 17 | Tank release valve |
| 18 | Overflow valve |
| 19 | Permeate tank |
| 20 | Permeate supply pump |
| 21 | Dialysis devices |
| 22 | Conductivity monitor bypass branch |
| 23 | Safety valve water inlet pressure |
| 24 | Heat exchanger tank |
| 25 | Temperature and conductivity meter tank outlet |
| 26 | Flow meter |
| 27 | Heat exchanger with temperature measuring and control device |
| 28 | Permeate return line |
| 29 | Emergency operation valve $1^{st}$ stage |
| 30 | Bidirectional valve emergency operation and hot cleaning membranes |
| 31 | Overflow tank |
| 32 | Emergency operation valve $2^{nd}$ stage |
| 33 | Emergency operation release valve |
| 34 | Safety valve emergency operation and emptying valve tank |
| 35 | Blocking valve emergency operation |
| 36 | Conductivity and temperature monitor emergency operation |
| 37 | Discharge collector |
| 38 | Metered addition disinfectant |
| 39 | Emergency supply conduit |
| 40 | Heater |
| 41 | Permeate sample removal |
| 42 | Loop flow pipe |
| 43 | Venturi suction |
| 44 | Tank inlet |

-continued

| | |
|---|---|
| 45 | Outlet passages tank inlet |
| 46 | Outlet groove |
| 47 | Cyclone prevention |
| 48 | Non-return valve |
| 49 | Inlet flow distributor |
| 50 | Circulation conduit |
| 51 | Flow distributor |
| 52 | Membrane support springs |
| 53 | Permeate collector plug |
| 54 | Module block |
| 55 | Module base plate |
| 56 | Module pipe flange plate |
| 57 | Fastening screws |
| 58 | Module pipe |
| 59 | Sealing nut module pipe |
| 60 | Spring centering |
| 61 | Pump connection |
| 62 | Permeate collector |
| 63 | Module head |
| 64 | Membrane non-return valve |
| 65 | Permeate connector |
| 66 | Clamp connection |
| 67 | Module head inner cone |
| 68 | Membrane concentrate outlet |
| 69 | Disinfectant suction plug with contact |
| 70 | Electrical/electronic assembly |
| 71 | Pallets frame |
| 72 | Module head seal top |
| 73 | Module head seal bottom |
| 74 | Module head abutment |
| 75 | Permeate collector and sample removal block |
| 76 | Non-return ball |
| 77 | Concentrate inlet |
| 78 | Module pipe flange |
| 79 | Flow meter hot cleaning membranes and bypass conduit monitor |
| 80 | Loop pressure monitor |
| 81 | Permeate removal block and sample permeate flow pipe |
| 82 | Tank emptying |
| 83 | Permeate $1^{st}$ stage |
| 84 | Permeate $2^{nd}$ stage |
| 85 | Permeate return conduit |
| 86 | Module pipe sealing ring |
| 87 | Annular gap |
| 88 | Fastening abutment module head |
| 89 | Fastening permeate collector block |
| 90 | Further conduit |
| 91 | Bypass conduit |

The invention claimed is:

1. A reverse osmosis system with at least one high pressure pump, which supplies untreated water to at least one module pipe, in which a membrane with a permeate collecting pipe is arranged, the system comprising:
 a permeate outlet of the at least one module pipe is connected by means of a first conduit to a permeate tank, which is in communication by means of a further conduit, connected into which is a permeate supply pump, to a loop feed line, connected to which is a plurality of dialysis devices, and that branching off from the first conduit there is a bypass conduit including a bypass valve that is located between the permeate outlet and the plurality of dialysis devices, which discharges into the further conduit downstream of the permeate tank and the permeate supply pump so that the permeate bypasses the permeate tank and the permeate supply pump, and flows directly to the plurality of dialysis devices.

2. A reverse osmosis system as claimed in claim 1, wherein the bypass conduit is provided with an overflow valve and a bidirectional valve.

3. A reverse osmosis system as claimed in claim 1, wherein a respective high pressure pump is arranged in a first and a subsequent second stage before two respective module pipes with membranes, that the permeate outlet of the first stage is connected to the second high pressure pump, that the permeate outlet of the second stage is connected to the permeate tank and that both permeate outlets are connectable by means of bypass conduits to the loop feed line.

4. A reverse osmosis system as claimed in claim 1, wherein the permeate tank is provided with a heating device, with which the permeate is heatable up to 37° C.

5. A reverse osmosis system as claimed in claim 4, wherein the permeate tank is of double-walled construction.

6. A reverse osmosis system as claimed in claim 4, wherein the heating device is a heat exchanger, the heat transfer medium of which is heatable with primary energy.

7. A reverse osmosis system as claimed in claim 6, wherein the heat transfer medium is heatable with gas.

8. A reverse osmosis system as claimed in claim 1, wherein arranged at the outlet of the permeate tank there is a cyclone preventer, which prevents the formation of a cyclone or the introduction of air into the outlet.

9. A reverse osmosis system as claimed in claim 1, wherein the permeate tank has a capacity of at most 200 l.

10. A reverse osmosis system as claimed in claim 9 wherein the permeate tank has a capacity of 100 to 120 l.

11. A reverse osmosis system with at least one high pressure pump, which supplies untreated water to at least one module pipe, in which a membrane with a permeate collecting pipe is arranged, the system comprising:
 a permeate outlet of the at least one module pipe is connected by means of a first conduit to a permeate tank, which is in communication by means of a further conduit, connected into which is a permeate supply pump, to a loop feed line, connected to which is a plurality of dialysis devices, and that branching off from the first conduit there is a bypass conduit including a bypass valve that is located between the permeate outlet and the plurality of dialysis devices, which discharges into the further conduit downstream of the permeate tank and the permeate supply pump so that the permeate bypasses the permeate tank and the permeate supply pump, and flows directly to the plurality of dialysis devices,
 wherein the bypass conduit is provided with an overflow valve and a bidirectional valve.

* * * * *